US011783564B2

(12) United States Patent
Leizerson et al.

(10) Patent No.: US 11,783,564 B2
(45) Date of Patent: Oct. 10, 2023

(54) CONTACTLESS PARAMETERS MEASUREMENT SYSTEM AND METHOD

(71) Applicant: Elbit Systems C4I and Cyber Ltd., Netanya (IL)

(72) Inventors: Ilya Leizerson, Netanya (IL); Reuven Dahan, Netanya (IL); Yaron Mayerowicz, Netanya (IL); Aviv Elisha, Netanya (IL)

(73) Assignee: Elbit Systems C4I and Cyber Ltd., Netanya (IL)

( * ) Notice: Subject to any disclaimer, the term of this patent is extended or adjusted under 35 U.S.C. 154(b) by 0 days.

(21) Appl. No.: 18/065,638

(22) Filed: Dec. 14, 2022

(65) Prior Publication Data
US 2023/0112404 A1 Apr. 13, 2023

Related U.S. Application Data

(63) Continuation of application No. PCT/IL2021/050735, filed on Jun. 17, 2021.

(30) Foreign Application Priority Data

Jun. 18, 2020 (IL) .......................................... 275524

(51) Int. Cl.
*G06V 10/25* (2022.01)
*G06T 7/33* (2017.01)
(Continued)

(52) U.S. Cl.
CPC ............ *G06V 10/25* (2022.01); *G06T 7/0012* (2013.01); *G06T 7/20* (2013.01); *G06T 7/337* (2017.01);
(Continued)

(58) Field of Classification Search
None
See application file for complete search history.

(56) References Cited

U.S. PATENT DOCUMENTS 10,416,076 B2 * 9/2019 Sandsten .................. G06T 5/50
11,402,273 B2 * 8/2022 Beall ..................... G01J 5/0205
(Continued)

FOREIGN PATENT DOCUMENTS

CN 101972140 A 2/2011
RU 175695 U1 12/2017
(Continued)

OTHER PUBLICATIONS

Contactless respiration monitoring using a 3D camera system, Author: Peter Nijholt 0654486; Dec. 2016.
(Continued)

*Primary Examiner* — Nancy Bitar

(57) ABSTRACT

A system for measuring temperature of one or more subjects within a scene including a reference object having an unknown emissivity, having an ambient temperature, the system comprising: a visible spectrum camera capable of acquiring images of the scene comprising (a) at least a Region of Interest (RoI) of each of the subjects, and (b) the reference object; a thermal image sensor capable of acquiring images of the scene comprising (a) at least the RoI of each of the subjects, and (b) the reference object; and a processing circuitry configured to: obtain (a) a visible spectrum image captured by the visible spectrum camera, and (b) a thermal image captured by the thermal image sensor, and (c) an indication of a scene ambient temperature within the scene; register the visible spectrum image and the thermal image onto a common coordinate system; identify (a) RoI pixels, on the common coordinate system, of the RoIs of the subjects within the visible spectrum image, (b) reference object pixels, on the common coordinate system, of the
(Continued)

reference object within the visible spectrum image and (c) a parameter correlated to an emissivity of the reference object, based on the reference temperature and on the indication of the scene ambient temperature; determine (a) RoI temperatures by analyzing respective RoIs pixels on the thermal image, and (b) a reference temperature by analyzing the reference object pixels on the thermal image; and upon existence of a difference between the reference temperature and the scene ambient temperature, correct the RoI temperatures, based on the difference and utilizing the parameter, to compensate for the difference, giving rise to corrected RoI temperatures.

20 Claims, 7 Drawing Sheets

(51) Int. Cl.
 *G06T 7/20* (2017.01)
 *G06T 7/00* (2017.01)
(52) U.S. Cl.
 CPC ........... *G06T 2207/10048* (2013.01); *G06T 2207/30201* (2013.01)

(56) References Cited

U.S. PATENT DOCUMENTS

| | | | |
|---|---|---|---|
| 11,635,331 B2* | 4/2023 | Beall | G01J 5/0025 374/121 |
| 2001/0046316 A1 | 11/2001 | Miyano et al. | |
| 2004/0208230 A1 | 10/2004 | Lee et al. | |
| 2006/0104488 A1 | 5/2006 | Bazakos et al. | |
| 2006/0193498 A1 | 8/2006 | Hartlove | |
| 2006/0232675 A1 | 10/2006 | Chamberlain et al. | |
| 2007/0153871 A1 | 7/2007 | Fraden | |
| 2008/0154138 A1 | 6/2008 | McQuilkin | |
| 2012/0289850 A1 | 11/2012 | Xu et al. | |
| 2013/0342691 A1* | 12/2013 | Lewis | H04N 7/18 348/143 |
| 2014/0368640 A1 | 12/2014 | Strandemar et al. | |
| 2016/0217672 A1 | 7/2016 | Yoon et al. | |
| 2018/0053392 A1 | 2/2018 | White et al. | |
| 2018/0143318 A1 | 5/2018 | Skowronek et al. | |
| 2018/0260680 A1 | 9/2018 | Finkelstein et al. | |
| 2018/0302555 A1* | 10/2018 | Chew | G01J 5/0275 |
| 2018/0333102 A1 | 11/2018 | De Haan et al. | |
| 2019/0187019 A1* | 6/2019 | Ekeroth | G01N 21/3504 |
| 2019/0321719 A1 | 10/2019 | Gillian et al. | |
| 2019/0374132 A1 | 12/2019 | Zalevsky et al. | |
| 2020/0105407 A1 | 4/2020 | Soreefan et al. | |
| 2020/0116583 A1* | 4/2020 | Hedberg | H04N 5/33 |
| 2020/0177825 A1 | 6/2020 | Kitayama et al. | |
| 2020/0242792 A1* | 7/2020 | Liu | G06T 7/593 |
| 2021/0302234 A1* | 9/2021 | Beall | G01J 5/0025 |

FOREIGN PATENT DOCUMENTS

| | | |
|---|---|---|
| RU | 177706 U1 | 3/2018 |
| WO | 2014012070 A1 | 1/2014 |
| WO | 2015086855 A1 | 6/2015 |
| WO | 2019162459 A1 | 8/2019 |

OTHER PUBLICATIONS

Development of a non-contact screening system for rapid medical inspection at a quarantine depot using a laser Doppler blood-flow meter, microwave radar and infrared thermography; ISSN: 0309-1902 (Print) 1464-522X (Online) Journal homepage: https://www.tandfonline.com/loi/ijmt20; Journal of Medical Engineering & Technology; T. Matsui, S. Suzuki, K. Ujikawa, T. Usui, S. Gotoh, M. Sugamata, Z. Badarch & S. Abe; Published online: Jul. 21, 2009.
Measurement system based on RBG camera signal for contactless breathing pattern and respiratory rate monitoring; Carlo Massaroni, Emiliano, Fabrizio Taffoni, Mario Merone; 978-1-5386-3392-2/18/ $31.00 © 2018 IEEE.
Monitoring of Cardiorespiratory Signals Using Thermal Imaging: A Pilot Study on Healthy Human Subjects; Carina Barbosa Pereira, Michael Czaplik, Vladimir Blazek, Steffen Leonhardt and Daniel Teichmann, Received: Apr. 5, 2018; Accepted: May 8, 2018; Published: May 13, 2018, www.mdpi.com/journal/sensors.
Multi-Spectral Facial Biometrics in Access Control; K. Lai, S. Samoil, and S.N. Yanushkevich; Department of Electrical and Computer Engineering, Biometric Technologies Laboratory, University of Calgary, 2500 University Drive NW, Calgary, Alberta, T2N 1N4 Canada, Email: {kelai,ssamoil,syanshk}@ucalgary.ca.

* cited by examiner

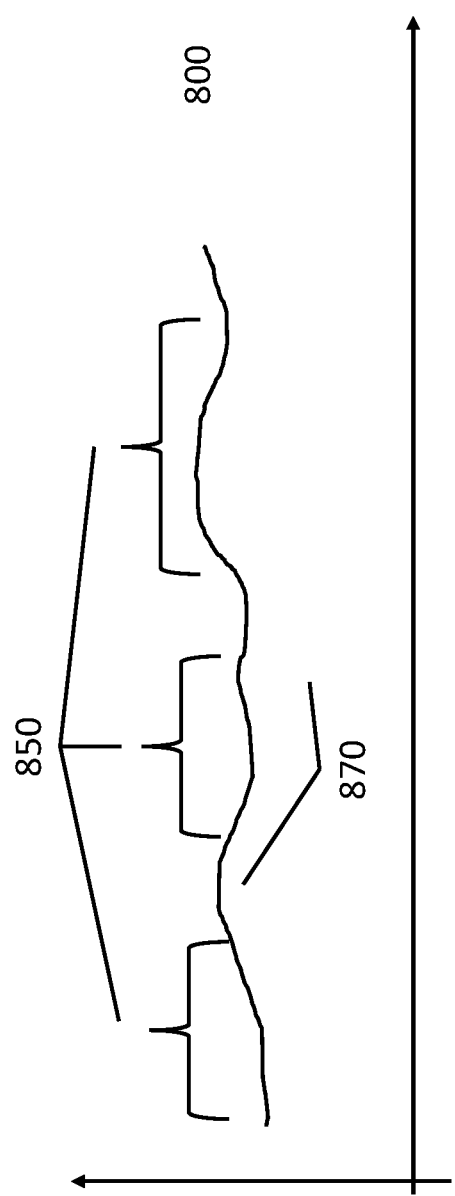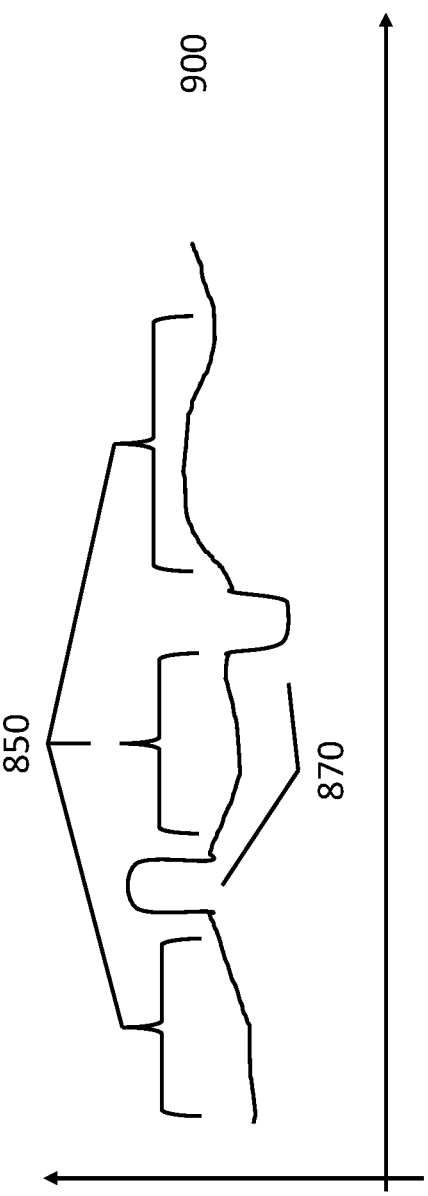

CONTACTLESS PARAMETERS MEASUREMENT SYSTEM AND METHOD

TECHNICAL FIELD

The invention relates to a system and method for usage of high accuracy contactless temperature measurement for determination of physiological body parameters.

BACKGROUND

Current contactless monitoring solutions utilize visual and thermal imagery for the measurement of body temperature and other medical indicators in order to help detect individuals that may be sick.

These current contactless monitoring systems require highly accurate and expensive sensors or to compromise on worse performances using low cost sensors. Therefore, current low-cost systems are not easily adapted to operate in changing environmental conditions.

There is thus a need in the art for a new body parameters measurement system and method.

References considered to be relevant as background to the presently disclosed subject matter are listed below. Acknowledgement of the references herein is not to be inferred as meaning that these are in any way relevant to the patentability of the presently disclosed subject matter.

WIPO International application No. 2019/162459 (MACNEISH et al.) published on Aug. 29, 2019, discloses a physiological monitoring apparatus (100) and methods are disclosed. A physiological monitor includes imaging sensors (120, 122, 124, 126), one of which is a time-of-flight imaging sensor (122). The physiological monitor (100) also includes a processing device (130) to receive data streams from the imaging sensors (120, 122, 124, 126). The processing device (130) may then extract time parameter data from the data streams, identify a physiological parameter from the extracted parameter data, and provide an indication of the physiological parameter.

MULTI-SPECTRAL FACIAL BIOMETRICS IN ACCESS CONTROL (Lai et al.) published on December, 2014, discloses how facial biometrics, acquired using multispectral sensors, such as RGB, depth, and infrared, assist the data accumulation in the process of authorizing users of automated and semi-automated access systems. This data serves the purposes of person authentication, as well as facial temperature estimation. We utilize depth data taken using an inexpensive RGB-D sensor to find the head pose of a subject. This allows the selection of video frames containing a frontal-view head pose for face recognition and face temperature reading. Usage of the frontal-view frames improves the efficiency of face recognition while the corresponding synchronized IR video frames allow for more efficient temperature estimation for facial regions of interest.

WIPO International application No. 2015/086855 (BORNAND et al.) published on Jun. 18, 2015, discloses a tracking system comprising one or more cameras adapted to take images, one or more data processing units, said tracking system further comprising one or more output or display units, wherein said camera is adapted to observe a geographical area of interest, wherein said one or more data processing unit is configured to detect a moving entity in the area of interest, to identify a reference zone in at least some of said images, wherein said reference zone is on or associated with said moving entity, and to analyze the reference zone in order to determine at least one parameter associated with said moving entity.

US Patent application No. 2019/0321719 (Gillian et al.) published on Oct. 24, 2019, discloses apparatuses and techniques for radar-enabled sensor fusion. In some aspects, a radar field is provided and reflection signals that correspond to a target in the radar field are received. The reflection signals are transformed to provide radar data, from which a radar feature indicating a physical characteristic of the target is extracted. Based on the radar features, a sensor is activated to provide supplemental sensor data associated with the physical characteristic. The radar feature is then augmented with the supplemental sensor data to enhance the radar feature, such as by increasing an accuracy or resolution of the radar feature. By so doing, performance of sensor-based applications, which rely on the enhanced radar features, can be improved.

US Patent application No. 2018/0260680 (FINKELSTEIN et al.) published on Sep. 13, 2018, discloses intelligent assistant devices and methods for interacting with a user are disclosed. In some examples, a method for interacting with a user comprises predicting suggested action(s) for the user and displaying the action(s) via a display of the device. While the suggested action(s) are displayed, audio input comprising a command followed by a keyword is received from the user. The audio input is processed locally on the intelligent assistance device to (1) determine that the keyword follows the command and (2) recognize that the command applies to the suggested action(s). Based on determining that the keyword follows the command and recognizing that the command applies to the suggested action(s), a user selection of the suggested action(s) is established. Based on establishing the user selection, the one or more suggested actions are executed.

US Patent application No. 2018/0143318 (Skowronek el al.) published on May 24, 2018, discloses a passive-tracking system is described herein. The system can include a visible-light sensor, a sound transducer, a thermal sensor, a time-of-flight (ToF) sensor, and a processor. The processor can receive visible-light frames from the visible-light sensor, sound frames from the sound transducer, thermal frames from the thermal sensor, and modulated-light frames from the ToF sensor. The processor, based on data of the visible-light and temperature frames, can also determine that an object is a living being and can provide an X and Y position of the object. The processor, based on data of the sound and positioning frames, can determine a Z position of the object. The X, Y, and Z positions may combine to form a three-dimensional (3D) position of the object. The processor can also passively track the object over time by selectively updating the 3D position of the object.

GENERAL DESCRIPTION

In accordance with a first aspect of the presently disclosed subject matter, there is provided a system for measuring temperature of one or more subjects within a scene including a reference object having an unknown emissivity, having an ambient temperature, the system comprising: a visible spectrum camera capable of acquiring images of the scene comprising (a) at least a Region of Interest (RoI) of each of the subjects, and (b) the reference object; a thermal image sensor capable of acquiring images of the scene comprising (a) at least the RoI of each of the subjects, and (b) the reference object; and a processing circuitry configured to: obtain (a) a visible spectrum image captured by the visible spectrum camera, and (b) a thermal image captured by the thermal image sensor, and (c) an indication of a scene ambient temperature within the scene; register the visible spectrum image and the thermal image onto a common coordinate system; identify (a) RoI pixels, on the common coordinate system, of the RoIs of the subjects within the visible spectrum image, (b) reference object pixels, on the common coordinate system, of the reference object within the visible spectrum image and (c) a parameter correlated to an emissivity of the reference object, based on the reference temperature and on the indication of the scene ambient temperature; determine (a) RoI temperatures by analyzing respective RoIs pixels on the thermal image, and (b) a reference temperature by analyzing the reference object pixels on the thermal image; and upon existence of a difference between the reference temperature and the scene ambient temperature, correct the RoI temperatures, based on the difference and utilizing the parameter, to compensate for the difference, giving rise to corrected RoI temperatures.

In some cases, the determination of the parameter correlated to the emissivity of the reference object is performed by analyzing the reference temperature and the indication of the scene ambient temperature at a plurality of point in time during a given time period.

In some cases, the system further comprising a three-dimensional (3D) camera capable of acquiring images of the scene comprising (a) at least a Region of Interest (RoI) of each of the subjects, and (b) the reference object, and wherein the processing circuitry is further configured to: obtain a depth image captured by the 3D camera; and utilize the depth image for the registration of the visible spectrum image and the thermal image onto the common coordinate system.

In some cases, the correction of the RoI temperatures is also based on at least one of: (a) a distance of the respective subject from the thermal image sensor determined based on the analysis of the depth image, or (b) on ambient moisture level.

In some cases, the indication of the ambient moisture level of is obtained from a moisture measuring device.

In some cases, the indication of the scene ambient temperature is obtained from a thermometer measuring ambient temperature within the scene.

In some cases, the thermal image sensor is uncooled.

In some cases, the visible spectrum camera has a spatial resolution higher than 2 mm/pixel.

In some cases, the thermal spectrum camera has a spatial resolution higher than 2 mm/pixel.

In some cases, the subjects are living subjects.

In some cases, the RoI is a body part of a body of the subject.

In some cases, the subjects are animals and wherein the RoI is one or more of: a body part of a body of the respective animal subject, a face of the respective animal subject, a forehead of the respective animal subject, or a mouth of the respective animal subject.

In some cases, the animals are human beings.

In some cases, the subjects are plants and wherein the RoI is one or more of: a leaf of the respective plant subject, or a fruit of the respective plant subject.

In some cases, the subjects are machines and wherein the RoI is an engine of the respective machine subject.

In some cases, the reference object is diffusive and not specular.

In some cases, the processing circuitry is further configured to alert an operator of the system upon identifying subjects associated with corrected RoI temperatures exceeding a threshold.

In some cases, the reference object is made of material which temperature changes in a known manner according to changes to the scene ambient temperature.

In some cases, the RoI is an area affected by breathing of the respective subject and wherein the processing circuitry is further configured to: obtain (a) a first sequence of subsequent visible spectrum images captured by the visible spectrum camera subsequently to the visible spectrum image, and (b) a second sequence of subsequent thermal images captured by the thermal image sensor subsequently to the thermal image; register the subsequent visible spectrum images and the subsequent thermal images onto the common coordinate system; identify subsequent RoI pixels, on the common coordinate system, of the RoIs of the subjects within the subsequent visible spectrum images; track the subsequent RoI pixels within the subsequent thermal images of the second sequence utilizing the respective subsequent visible spectrum images of the first sequence; and determine a respiratory rate of the respective subject by analyzing the tracked subsequent RoI pixels.

In some cases, the RoI is a forehead of the respective subject and wherein the processing circuitry is further configured to: obtain a third sequence of subsequent visible spectrum images captured by the visible spectrum camera subsequently to the visible spectrum image; track the RoI within the subsequent visible spectrum images of the third sequence; and determine a pulse of the respective subject by analyzing changes of color within the RoI.

In some cases, the reference object includes one or more symbols visible to the visible spectrum camera or to the thermal image sensor and wherein the reference object pixels are identified using at least one of the symbols.

In accordance with a second aspect of the presently disclosed subject matter, there is provided a method for measuring temperature of one or more subjects within a scene including a reference object having an unknown emissivity, having an ambient temperature, the method comprising: obtaining, by a processing circuitry. (a) a visible spectrum image captured by a visible spectrum camera capable of acquiring images of the scene comprising at least a Region of Interest (RoI) of each of the subjects, and the reference object, and (b) a thermal image captured by a thermal image sensor capable of acquiring images of the scene comprising at least the RoI of each of the subjects, and the reference object, and (c) an indication of a scene ambient temperature within the scene; registering, by the processing circuitry, the visible spectrum image and the thermal image onto a common coordinate system; identifying, by the processing circuitry, (a) RoI pixels, on the common coordinate system, of the RoIs of the subjects within the visible spectrum image, and (b) reference object pixels, on the common coordinate system, of the reference object within the visible spectrum image; determining, by the processing circuitry, (a) RoI temperatures by analyzing respective RoIs pixels on the thermal image, (b) a reference temperature by analyzing the reference object pixels on the thermal image and (c) a parameter correlated to an emissivity of the reference object, based on the reference temperature and on the indication of the scene ambient temperature; and upon existence of a difference between the reference temperature and the scene ambient temperature, correcting, by the processing circuitry, the RoI temperatures, based on the difference and utilizing the parameter, to compensate for the difference, giving rise to corrected RoI temperatures.

In some cases, the determination of the parameter correlated to the emissivity of the reference object is performed by analyzing the reference temperature and the indication of the scene ambient temperature at a plurality of point in time during a given time period.

In some cases, the method further comprising: obtaining, by the processing circuitry, a depth image captured by a three-dimensional (3D) camera capable of acquiring images of the scene comprising (a) at least a Region of Interest (RoI) of each of the subjects, and (b) the reference object; and utilizing, by the processing circuitry, the depth image for the registration of the visible spectrum image and the thermal image onto the common coordinate system.

In some cases, the correction of the RoI temperatures is also based on at least one of: (a) a distance of the respective subject from the thermal image sensor determined based on the analysis of the depth image, or (b) on ambient moisture level.

In some cases, the indication of the ambient moisture level of is obtained from a moisture measuring device.

In some cases, the indication of the scene ambient temperature is obtained from a thermometer measuring ambient temperature within the scene.

In some cases, the thermal image sensor is uncooled.

In some cases, the visible spectrum camera has a spatial resolution higher than 2 mm/pixel.

In some cases, the thermal spectrum camera has a spatial resolution higher than 2 mm/pixel.

In some cases, the subjects are living subjects.

In some cases, the RoI is a body part of a body of the subject.

In some cases, the subjects are animals and wherein the RoI is one or more of: a body part of a body of the respective animal subject, a face of the respective animal subject, a forehead of the respective animal subject, or a mouth of the respective animal subject.

In some cases, the animals are human beings.

In some cases, the subjects are plants and wherein the RoI is one or more of: a leaf of the respective plant subject, or a fruit of the respective plant subject.

In some cases, the subjects are machines and wherein the RoI is an engine of the respective machine subject.

In some cases, the reference object is diffusive and not specular.

In some cases, the method further comprising alerting, by the processing circuitry, an operator of the system upon identifying subjects associated with corrected RoI temperatures exceeding a threshold.

In some cases, the reference object is made of material which temperature changes in a known manner according to changes to the scene ambient temperature.

In some cases, the RoI is an area affected by breathing of the respective subject and wherein method further comprising: obtaining, by the processing circuitry, (a) a first sequence of subsequent visible spectrum images captured by the visible spectrum camera subsequently to the visible spectrum image, and (b) a second sequence of subsequent thermal images captured by the thermal image sensor subsequently to the thermal image; registering, by the processing circuitry, the subsequent visible spectrum images and the subsequent thermal images onto the common coordinate system; identifying, by the processing circuitry, subsequent RoI pixels, on the common coordinate system, of the RoIs of the subjects within the subsequent visible spectrum images; tracking, by the processing circuitry, the subsequent RoI pixels within the subsequent thermal images of the second sequence utilizing the respective subsequent visible spectrum images of the first sequence; and determining, by the processing circuitry, a respiratory rate of the respective subject by analyzing the tracked subsequent RoI pixels.

In some cases, the RoI is a forehead of the respective subject and wherein the method further comprising: obtaining, by the processing circuitry, a third sequence of subsequent visible spectrum images captured by the visible spectrum camera subsequently to the visible spectrum image; tracking, by the processing circuitry, the RoI within the subsequent visible spectrum images of the third sequence; and determining, by the processing circuitry, a pulse of the respective subject by analyzing changes of color within the RoI.

In some cases, the reference object includes one or more symbols visible to the visible spectrum camera or to the thermal image sensor and wherein the reference object pixels are identified using at least one of the symbols.

In accordance with a third aspect of the presently disclosed subject matter, there is provided a non-transitory computer readable storage medium having computer readable program code embodied therewith, the computer readable program code, executable by at least one processing circuitry of a computer to perform a method for measuring temperature of one or more subjects within a scene including a reference object having an unknown emissivity, having an ambient temperature, the method comprising: obtaining, by a processing circuitry, (a) a visible spectrum image captured by a visible spectrum camera capable of acquiring images of the scene comprising at least a Region of Interest (RoI) of each of the subjects, and the reference object, and (b) a thermal image captured by a thermal image sensor capable of acquiring images of the scene comprising at least the RoI of each of the subjects, and the reference object, and (c) an indication of a scene ambient temperature within the scene; registering, by the processing circuitry, the visible spectrum image and the thermal image onto a common coordinate system; identifying, by the processing circuitry, (a) RoI pixels, on the common coordinate system, of the RoIs of the subjects within the visible spectrum image, and (b) reference object pixels, on the common coordinate system, of the reference object within the visible spectrum image; determining, by the processing circuitry, (a) RoI temperatures by analyzing respective RoIs pixels on the thermal image, (b) a reference temperature by analyzing the reference object pixels on the thermal image and (c) a parameter correlated to an emissivity of the reference object, based on the reference temperature and on the indication of the scene ambient temperature; and upon existence of a difference between the reference temperature and the scene ambient temperature, correcting, by the processing circuitry, the RoI temperatures, based on the difference and utilizing the parameter, to compensate for the difference, giving rise to corrected RoI temperatures.

BRIEF DESCRIPTION OF THE DRAWINGS

In order to understand the presently disclosed subject matter and to see how it may be carried out in practice, the subject matter will now be described, by way of non-limiting examples only, with reference to the accompanying drawings, in which:

FIG. 8A depicts schematic records of a non-limiting example of reference object's temperature values; and FIG. 8B depict a non-limiting example of ambient temperature measurements, measured during a given time period.

DETAILED DESCRIPTION

Figure 1:
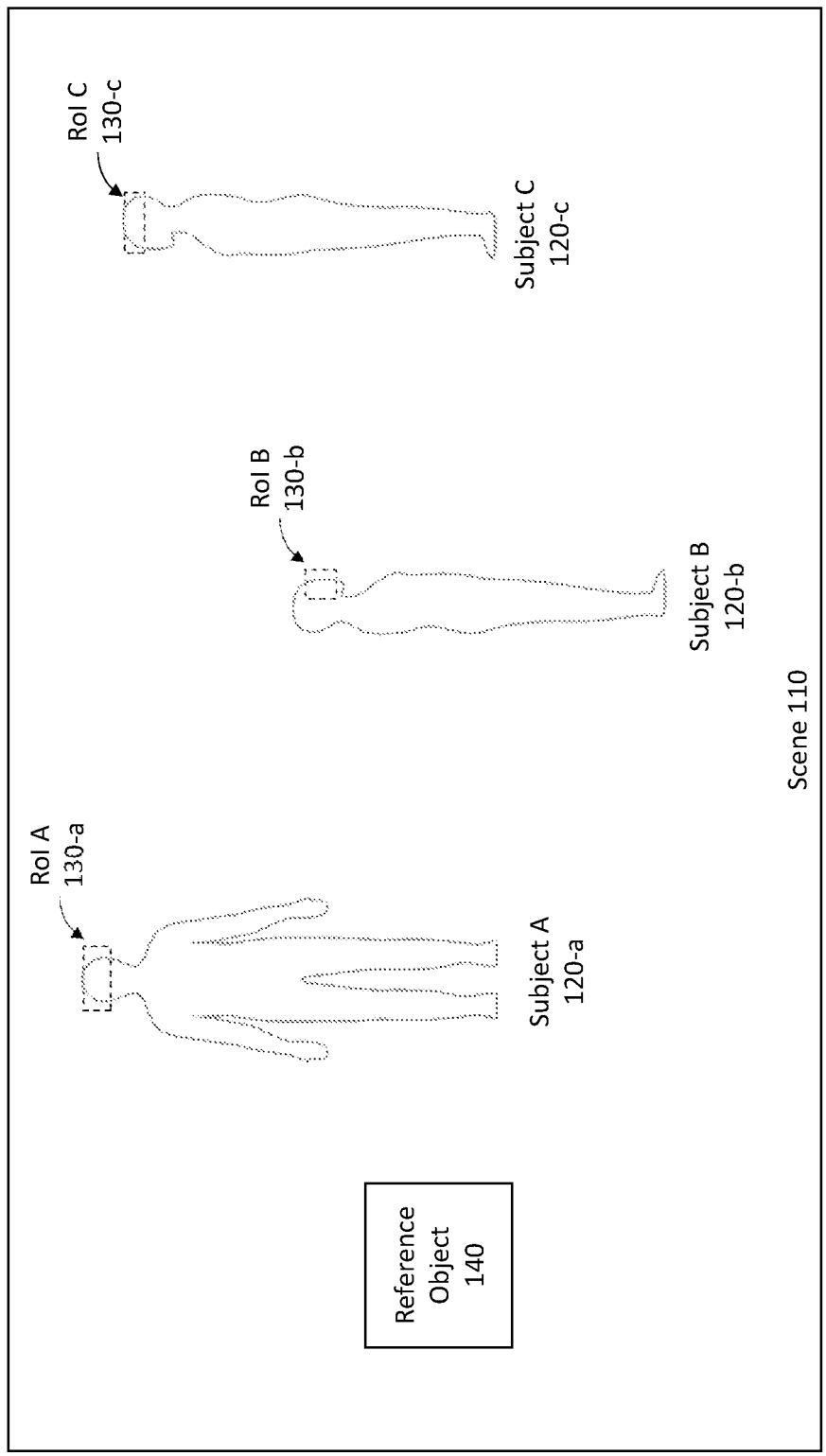
FIG. 1 is a schematic illustration of an example scene with one or more subjects and a reference object, in accordance with the presently disclosed subject matter.

In the following detailed description, numerous specific details are set forth in order to provide a thorough understanding of the presently disclosed subject matter. However, it will be understood by those skilled in the art that the presently disclosed subject matter may be practiced without these specific details. In other instances, well-known methods, procedures, and components have not been described in detail so as not to obscure the presently disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "obtaining", "registering", "identifying", "determining", "correcting", "tracking" or the like, include action and/or processes of a computer that manipulate and/or transform data into other data, said data represented as physical quantities, e.g. such as electronic quantities, and/or said data representing the physical objects. The terms "computer", "processor", "processing resource" and "controller" should be expansively construed to cover any kind of electronic device with data processing capabilities, including, by way of non-limiting example, a personal desktop/laptop computer, a server, a computing system, a communication device, a smartphone, a tablet computer, a smart television, a processor (e.g. digital signal processor (DSP), a microcontroller, a field programmable gate array (FPGA), an application specific integrated circuit (ASIC), etc.), a group of multiple physical machines sharing performance of various tasks, virtual servers co-residing on a single physical machine, any other electronic computing device, and/or any combination thereof.

The operations in accordance with the teachings herein may be performed by a computer specially constructed for the desired purposes or by a general-purpose computer specially configured for the desired purpose by a computer program stored in a non-transitory computer readable storage medium. The term "non-transitory" is used herein to exclude transitory, propagating signals, but to otherwise include any volatile or non-volatile computer memory technology suitable to the application.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus, the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

Figure 2:
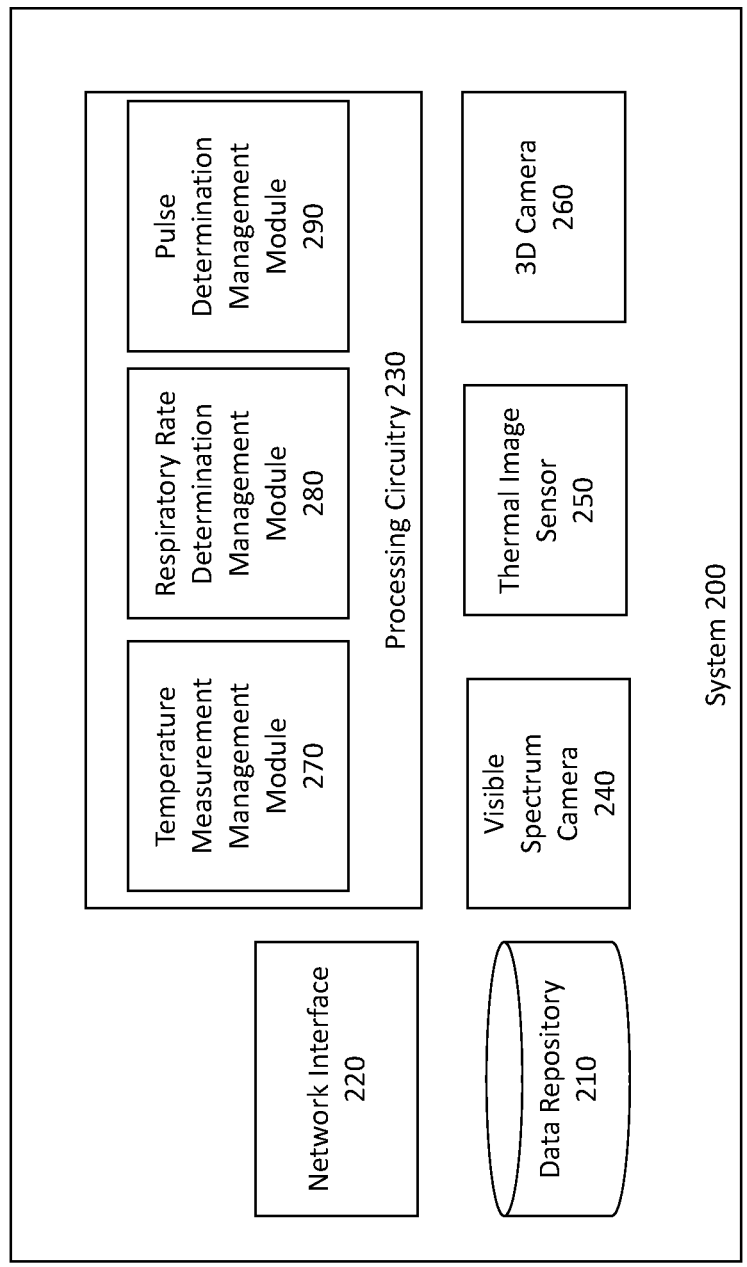
FIG. 2 is a block diagram schematically illustrating one example of a system for measuring temperature of one or more subjects within a scene, in accordance with the presently disclosed subject matter.
Figure 3:
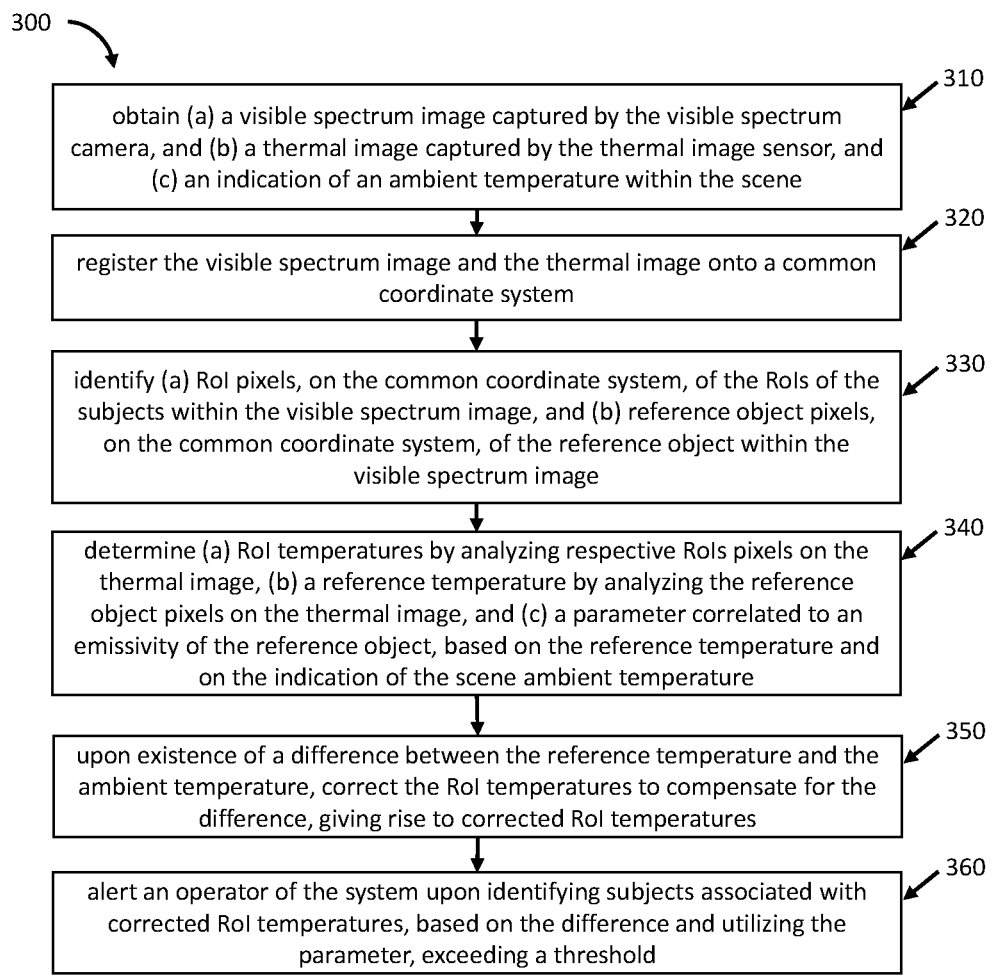
FIG. 3 is a flowchart illustrating one example of a sequence of operations carried out for temperature measurement, in accordance with the presently disclosed subject matter.
Figure 4:
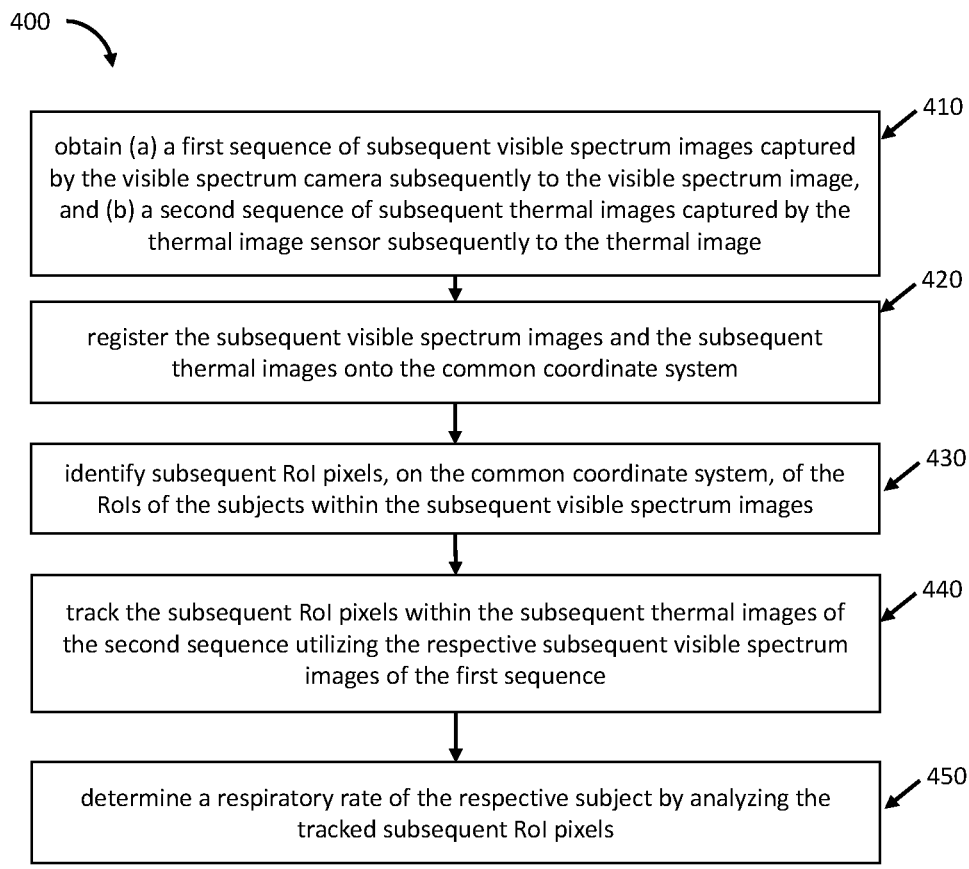
FIG. 4 is a flowchart illustrating one example of a sequence of operations carried out for respiratory rate determination, in accordance with the presently disclosed subject matter.
Figure 5:
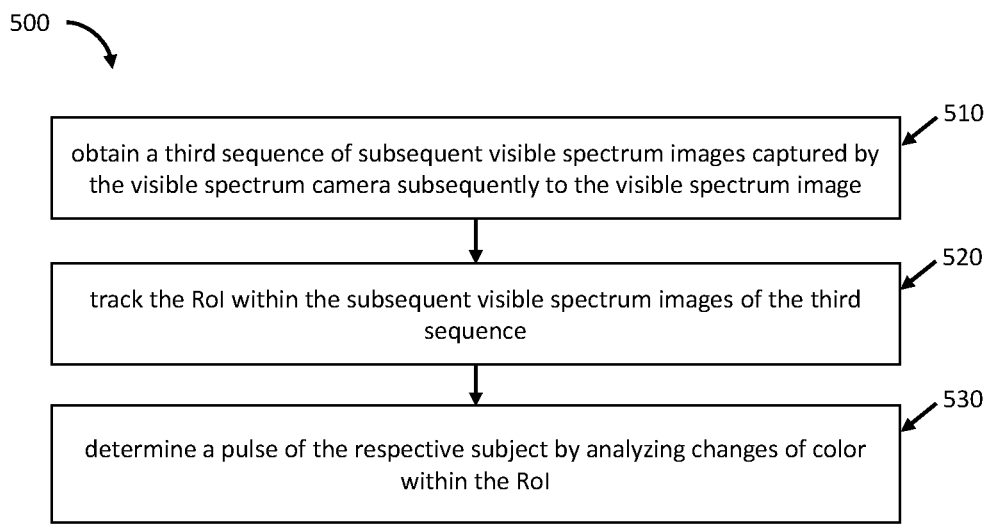
FIG. 5 is a flowchart illustrating one example of a sequence of operations carried out for pulse determination, in accordance with the presently disclosed subject matter.

In embodiments of the presently disclosed subject matter, fewer, more and/or different stages than those shown in FIGS. 3-5 may be executed. In embodiments of the presently disclosed subject matter one or more stages illustrated in FIGS. 3-5 may be executed in a different order and/or one or more groups of stages may be executed simultaneously. FIGS. 1-2 illustrate a general schematic of the system architecture in accordance with an embodiment of the presently disclosed subject matter. Each module in FIGS. 1-2 can be made up of any combination of software, hardware and/or firmware that performs the functions as defined and explained herein. The modules in FIGS. 1-2 may be centralized in one location or dispersed over more than one location. In other embodiments of the presently disclosed subject matter, the system may comprise fewer, more, and/or different modules than those shown in FIGS. 1-2.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

Bearing this in mind, attention is drawn to FIG. 1, a schematic illustration of an example scene with one or more subjects and a reference object, in accordance with the presently disclosed subject matter.

Scene 110 can include one or more subjects (e.g. subject A 120-a, subject B 120-b, subject C 120-c), the subjects can be human beings, animals, plants, machines or any other heat emitting objects. Scene 110 is viewable by one or more sensors. The sensors can take at least one image of scene 110 which includes at least part of the subjects and at least part of a reference objects 140. In some cases, at least parts of the subjects are Regions of Interest (RoIs) (e.g. RoI A 130-a, RoI B 130-*b*, RoI C 130-*c*). The RoIs can include a face of a respective subject, a forehead of the respective subject, a mouth of the respective subject or any other body part of the respective subject. A non-limiting example can be that subject A 120-*a* is a human being and RoI A 130-*a* includes at least an area of subject's A 120-*a* forehead.

Scene 110 can additionally include one or more reference objects 140. Reference object 140 can be made of material whose temperature changes in a known manner according to changes to the scene ambient temperature within scene 110. In some cases, the temperature of the reference object 140 is the scene ambient temperature. In some cases, the reference object 140 is at least part of a cardboard.

In some cases, the reference object 140 is diffusive and not specular, thus does not have mirror-like properties of wave reflection. It is to be noted that reference object 140 is not a black body.

In some cases, the reference object 140 includes one or more known symbols that are visible to a visible spectrum camera or to a thermal image sensor or to both the visible spectrum camera and the thermal image sensor, in some cases the known symbols are visible to the visible spectrum camera and not to the thermal image sensor, as further detailed herein, inter alia with reference to FIG. 3.

Scene 110 can be indoors, for example: a reception area of a medical practitioner, where patients await reception by the medical practitioner. In some cases, scene 110 is outdoors, for example: scene 110 can be part of a park where people and animals are roaming around. In some cases, scene 110 is a large space including a large number of subjects, for example, part of a busy airport or train station.

It is to be noted that the subjects within scene 110 can be stationary and/or moving within scene 110.

Having briefly described a scene with one or more subjects and a reference object, attention is drawn to FIG. 2, a block diagram schematically illustrating one example of a system for measuring temperature of one or more subjects within a scene, in accordance with the presently disclosed subject matter.

According to certain examples of the presently disclosed subject matter, system 200 comprises a visible spectrum camera 240. Visible spectrum camera 240 is capable of acquiring images of scene 110. Visible spectrum camera 240 can be made of one or more sensors capable of acquiring images in at least the visible spectrum. The one or more sensors can be spatially distributed to acquire images of scene 110 from one or more locations and/or from one or more viewpoints. In some cases, visible spectrum camera 240 is a high-definition camera, having a spatial resolution higher than 2 mm/pixel in the relevant object plane.

In addition, system 200 comprises a thermal image sensor 250. The thermal image sensor 250 is also capable of acquiring images of scene 110. In some cases, the thermal image sensor 250 is an infrared (IR) image sensor capable of acquiring images of scene 110 in at least the IR spectrum. In some cases, the thermal image sensor 250 is a near-infrared (NIR) image sensor capable of acquiring images of scene 110 in at least the NIR spectrum. Thermal image sensor 250 can be made of one or more sensors capable of acquiring images in at least the IR. The one or more thermal sensors can be spatially distributed to acquire thermal images of scene 110 from one or more locations and/or from one or more viewpoints. In some cases, the thermal image sensor 250 is an uncooled thermal image sensor.

System 200 can optionally comprise a three-dimensional (3D) camera 260. The 3D camera 260 is capable of acquiring 3D images of scene 110. In some cases, 3D camera 260 creates digital 3D representations of the subjects (e.g. subject A 120-*a*, subject B 120-*b*, subject C 120-*c*) and/or the objects located within the scene 110. In some cases, 3D camera 260 is a range camera capable of producing an image showing the distance to one or more points in scene 110 from a given location. In some cases, 3D camera 260 produces a point cloud of scene 110. 3D camera 260 can be made of one or more sensors capable of acquiring images of scene 110. The one or more sensors can be spatially distributed to acquire images of scene 110 from one or more locations and/or from one or more viewpoints. The 3D camera's 260 sensors can be one or more of: a Light Imaging, Detection, and Ranging (LiDAR) sensor, a stereoscopic sensor, a Time of Flight (ToF) sensor, or any combinations thereof.

System 200 can further comprise a network interface 220 enabling connecting the system 200 to a network and enabling it to send and receive data sent thereto through the network, including in some cases receiving information collected from one or more remote sensors, for example: receiving indication of the scene ambient temperature of scene 110 from a thermometer that is a location within scene 110. In some cases, the network interface 220 can be connected to a Local Area Network (LAN), to a Wide Area Network (WAN), or to the Internet. In some cases, the network interface 220 can connect to a wireless network.

System 200 can further comprise or be otherwise associated with a data repository 210 (e.g. a database, a storage system, a memory including Read Only Memory—ROM, Random Access Memory—RAM, or any other type of memory, etc.) configured to store data, including, inter alia, information defining the spatial location of the RoIs (e.g. RoI A 130-*a*, RoI B 130-*b*, RoI C 130-*c*) within scene 110, point clouds of subjects (e.g. subject A 120-*a*, subject B 120-*b*, subject C 120-*c*) and/or objects located within scene 110, scene ambient temperature, threshold temperatures, etc. In some cases, data repository 210 can be further configured to enable retrieval and/or update and/or deletion of the data stored thereon. It is to be noted that in some cases, data repository 210 can be distributed. It is to be noted that in some cases, data repository 210 can be stored in on cloud-based storage.

System 200 further comprises processing circuitry 230. Processing circuitry 230 can be one or more processing circuitry units (e.g. central processing units), microprocessors, microcontrollers (e.g. microcontroller units (MCUs)) or any other computing devices or modules, including multiple and/or parallel and/or distributed processing circuitry units, which are adapted to independently or cooperatively process data for controlling relevant system 200 resources and for enabling operations related to system 200 resources.

The processing circuitry 230 comprises one or more of the following modules: temperature measurement management module 270, respiratory rate determination management module 280, and pulse determination management module 290.

Temperature measurement management module 270 can be configured to perform a temperature measurement process, as further detailed herein, inter alia with reference to FIG. 3.

Respiratory rate determination management module 280 can be configured to perform a respiratory rate determination process, as further detailed herein, inter alia with reference to FIG. 4.

Pulse determination management module 290 can be configured to perform a pulse determination process, as further detailed herein, inter alia with reference to FIG. 5.

Turning to FIG. 3, there is shown a flowchart illustrating one example of a sequence of operations carried out for temperature measurement, in accordance with the presently disclosed subject matter.

According to certain examples of the presently disclosed subject matter, system 200 can be configured to perform a temperature measurement process 300, e.g. utilizing the temperature measurement management module 270.

For this purpose, system 200 can be configured to obtain (a) a visible spectrum image captured by the visible spectrum camera 240, and (b) a thermal image captured by the thermal image sensor 250, and (c) an indication of a scene ambient temperature within the scene 110 (block 310).

System 200 obtains a visible spectrum image of scene 110, which includes one or more subjects (e.g. subject A 120-*a*, subject B 120-*b*, subject C 120-*c*), and a reference object 140 having an ambient temperature. The visible spectrum image comprises at least part of an RoI (e.g. RoI A 130-*a*, RoI B 130-*b*, RoI C 130-*c*) of at least one of the subjects (e.g. one of: subject A 120-*a*, subject B 120-*b*, subject C 120-*c*), and the reference object 140. The visible spectrum image is captured by the visible spectrum camera 240.

System 200 can be configured to obtain a thermal image captured by the thermal image sensor 250. The thermal image comprises the at least RoI (e.g. RoI A 130-*a*, RoI B 130-*b*, RoI C 130-*c*) of each of the subjects (e.g. subject A 120-*a*, subject B 120-*b*, subject C 120-*c*) as comprised within the visible spectrum image. The thermal image also comprises the reference object 140.

System 200 can be configured to also obtain an indication of a scene ambient temperature within scene 110. In some cases, the indication of the scene ambient temperature can be obtained from a thermometer measuring ambient temperature within scene 110. The thermometer can be external to system 200 or comprised as part of system 200. In some cases, the indication of the scene ambient temperature can be received by system 200 from an external source, via a wired or wireless network by utilizing network interface 220. In some case, the indication of the scene ambient temperature can be determined by system 200 based on pre-defined properties of scene 110.

In a non-limiting example, system 200 obtains a visible spectrum image of scene 110 wherein RoI A 130-*a* of subject A 120-*a* and the reference object 140 are visible. System 200 also obtains a thermal image that comprises the thermal readings from RoI A 130-*a* and the thermal readings from reference object 140. System 200 also obtains an indication that the scene ambient temperature within scene 110 is 24 degrees Celsius.

After obtaining the visible spectrum image, the thermal image, system 200 can be further configured to register the visible spectrum image and the thermal image onto a common coordinate system (block 320). The registration of the visible spectrum image and the thermal image onto a common coordinate system enables system 200 to associate each pixel of the visible spectrum image to the corresponding pixel on the thermal image by utilizing the common coordinate system. In some cases, the registration of the visible spectrum image and the thermal image onto a common coordinate system is required because of parallax effect between the thermal image sensor 250 and the visible spectrum camera 240. The registration sustains variation of distance between the sensors (e.g. visible spectrum camera 240 and thermal image sensor 250) and subjects (e.g. subject A 120-*a*, subject B 120-*b*, subject C 120-*c* and/or the reference object 140).

In some cases, system 200 includes a 3D camera 260 capable of acquiring depth images of the scene 110 comprising the at least RoI (e.g. RoI A 130-*a*, RoI B 130-*b*, RoI C 130-*c*) of each of the subjects (e.g. subject A 120-*a*, subject B 120-*b*, subject C 120-*c*) as comprised within the visible spectrum image. The registration of the visible spectrum image and the thermal image onto a common coordinate system can include also utilizing the depth images of the scene 110 for the registration. In these cases, 3D camera 260 can obtain a depth image and system 200 can utilize the depth image for the registration of the visible spectrum image and the thermal image onto the common coordinate system in order to sustain variation of distance between the visible spectrum camera 240, the thermal image sensor 250, the 3D camera 260 and subjects (e.g. subject A 120-*a*, subject B 120-*b*, subject C 120-*c*) and/or the reference object 140 and/or the reference object 140. The distance dependent registration is required as different parts of scene 110 appear at different distance from visible spectrum camera 240, thermal image sensor 250 and from 3D camera 260. In some cases, a registration of the visible spectrum image, the thermal image and the depth image is required. In some cases, the registration can be a non-rigid registration. The registration utilizes the knowledge of the distance to each point in scene 110. In some cases, usage of 3D camera 260 enables system 200 to create a point cloud, in which each point in scene 110 is associated with coordinates (e.g. X, Y, Z coordinates) with respect to the location of the 3D camera 260. in some cases, the transformation of coordinates between different sensors (e.g. visible spectrum camera 240, thermal image sensor 250 and 3D camera 260) can be evaluated by a preliminary calibration procedure. The preliminary calibration procedure can be realized by utilizing one or more known calibration methods. One non-limiting example is capturing of a given geometric pattern (e.g. a black and white checkboard pattern) observed by all sensors (e.g. visible spectrum camera 240, thermal image sensor 250 and 3D camera 260) during substitution of the given geometric pattern in a number of orientations and distances with respect to the sensors (e.g. visible spectrum camera 240, thermal image sensor 250 and 3D camera 260) which can be rigidly mounted. Another exemplary method of a preliminary calibration process of the sensors (e.g. visible spectrum camera 240, thermal image sensor 250 and 3D camera 260) can be done by capturing an image of an object within scene 110 at one or more distances. This exemplary procedure allows an equivalence between the distance and the correct transformation of a point object from one of the sensor (e.g. one of: visible spectrum camera 240, thermal image sensor 250 and 3D camera 260) to another sensor (e.g. one of: visible spectrum camera 240, thermal image sensor 250 and 3D camera 260). The preliminary calibration methods enable system 200 to apply a correction of image aberrations. In some cases, the objects used for the preliminary calibration process are made from materials or are colored in a way that makes them observable by the sensors (e.g. visible spectrum camera 240, thermal image sensor 250 and 3D camera 260).

Continuing the above non-limiting example, system 200 registers the visible spectrum image and the thermal image onto a common coordination system. The registration allows a pixel-to-pixel correspondence between the pixels of the visible spectrum image and the pixels of the thermal image. In some cases, system 200 utilizes a depth image of scene 110 for the registration and the depth data may be registered with the visible and the thermal images.

After registering the visible spectrum image and the thermal image onto a common coordinate system, system 200 can be further configured to identify (a) RoI pixels, on the common coordinate system, of the RoIs (e.g. RoI A 130-*a*, RoI B 130-*b*, RoI C 130-*c*) of the subjects (e.g. subject A 120-*a*, subject B 120-*b*, subject C 120-*c*) within the visible spectrum image, and (b) reference object pixels, on the common coordinate system, of the reference object 140 within the visible spectrum image (block 330).

System 200 can identify RoI pixels, on the common coordinate system, of the RoIs (e.g. RoI A 130-*a*, RoI B 130-*b*, RoI C 130-*c*) of the subjects (e.g. subject A 120-*a*, subject B 120-*b*, subject C 120-*c*) within the visible spectrum image.

System 200 can be further configured to identify reference object pixels, on the common coordinate system, of the reference object 140 within the visible spectrum image.

The identification of the RoI pixels can be realized by system 200 by performing an analysis of the visible spectrum image. The RoI pixels can be for example pixels of the subject's (e.g. subject A 120-*a*, subject B 120-*b*, subject C 120-*c*) head or of the area of the forehead or nostrils. The reference object pixels are the pixels of the visible spectrum image containing at least part of the reference object 140.

In some cases, the identification of the reference object pixels is based on a known shape of the reference object 140. For example, the reference object 140 can have a specific rectangular shape and system 200 can analyze the visible spectrum image to identify the specific rectangular shape.

In some cases, the identification of the reference object pixels is based on a known location of the reference object 140 within scene 110. For example, the reference object 140 can be locates in a lower right corner of scene 110 with respect to visible spectrum camera 240 and system 200 can analyze the visible spectrum image to identify the specific rectangular shape in that location.

In some cases, the reference object 140 includes one or more known symbols that are visible to the visible spectrum camera and/or to the thermal image sensor. In some cases, reference object 140, is not visible to the thermal image sensor. In these cases, the identification of the reference object pixels can be realized by system 200 analyzing the visible spectrum image to identify at least one of the known symbols.

Continuing the above non-limiting example, RoI A 130-*a* is the forehead of subject A 120-*a*. System 200 identifies the RoI pixels, which in our example are the pixels of RoI A 130-*a* by utilizing a head determination algorithm on the visible spectrum image. The reference object 140 in our non-limiting example is a cardboard with a known symbol printed thereon. The symbol is visible to visible spectrum camera 240. System 200 identifies the reference object pixels by analyzing the visible spectrum image to identify the known symbol.

System 200 can be further configured to determine RoI temperatures by analyzing respective RoIs pixels on the thermal image and a reference temperature by analyzing the reference object pixels on the thermal image (block 340).

The RoI temperatures can be determined by system 200 by using the registration of both the visible spectrum image and the thermal image onto a common coordinate system to locate the RoIs pixels, which were identified by system 200 on the visible spectrum image, within the thermal image. These RoI pixels within the thermal image represent temperature of these RoIs (e.g. subject A 120-*a*, subject B 120-*b*, subject C 120-*c*) of the subjects (e.g. subject A 120-*a*, subject B 120-*b*, subject C 120-*c*) as measured by thermal image sensor 250.

Continuing the non-limiting example from above, system 200 can analyze the RoI pixels associated with RoI A 130-*a* to determine the RoI temperature of the forehead of subject A 120-*a* is 36 degrees Celsius. Thus, subject's A 120-*a* temperature seems to be normal.

Similarly, the reference temperature can be determined by system 200 by using the registration of both the visible spectrum image and the thermal image onto a common coordinate system to locate the reference object pixels, identified on the visible spectrum image by system 200, within the thermal image. These reference object pixels within the thermal image represent the temperature of the reference object 140 as registered by thermal image sensor 250.

Continuing the non-limiting example from above, system 200 can analyze the reference object pixels associated with the reference object 140 to determine the reference temperature to be 26 degrees Celsius.

Upon existence of a difference between the reference temperature and the scene ambient temperature, system 200 can be further configured to correct the RoI temperatures to compensate for the difference, giving rise to corrected RoI temperatures (block 350).

An exemplary mathematical expression of the correction used to correct the RoI temperatures to compensate for the difference can be the following expression:

$$Tobj\_2 = Tobj\_1 + (T'obj\_1 - T'obj\_2) - \alpha \cdot (Tref\_1 - Tref\_2) + f(Tamb\_2) - f(Tamb\_1)$$

Where the exemplary mathematical expression is formed by supposing that one of the measurements was taken at time t1 such that the following values are obtained by system 200:

Tobj_1—the real temperature of an object (the object can be for example one of: subject A 120-*a*, subject B 120-*b*, subject C 120-*c*) that can be measured by a golden standard equipment;

T'obj_1—the object temperature as it is measured by the thermal image sensor 250 in the pre-defined RoI;

Tamb_1—the scene ambient temperature; and

Tref_1—the temperature of the reference object 140 that is the same as the scene ambient temperature at the measurement moment t1.

System 200 obtains an additional measurement at time t2, as follows:

T'obj_2—object temperature as it is measured by the thermal image sensor 250 in the pre-defined RoI:

Tamb_2—scene ambient temperature at the time t2; and

Tref_2—temperature of the reference object 140 that is the same as the scene's ambient temperature at the measurement moment t2.

f(Tamb_1), f(Tamb_2) is a function for correction of the thermal image sensor 250 offset as a function of scene ambient temperature. This functionality may be embedded in the thermal imaging sensor 250 or may be supplied by its manufacturer. In case of f embedded in the reading of the thermal image sensor, the function f=0.

α is a calibration parameter describing the effect of the reference object's 140 temperature on the signal measured by the thermal image sensor 250.

The temperature at both moments t1 and t2 are at steady states.

Practically, α depends on emissivity of the reference object's 140 material. However, in majority of practical cases the emissivity of the reference object 140 cannot be measured, for example: because physical access to the reference object 140 is limited. In some embodiments α can be calculated during an adaptive calibration procedure of system 200. In this procedure, the ambient temperature values and the reference object's 140 temperature as it is measured by the thermal image sensor 250 are measured at a plurality of point in time during a given time interval during which the ambient temperature may change. In FIG. 8A we show schematic records of a non-limiting example of reference object's 140 temperature values 800, measured by the thermal image sensor 250 at a plurality of point in time during the given time period, and in FIG. 8B we depict the ambient temperature measurements 900, measured during the same given time period. FIGS. 8A and 8B demonstrate the variations of readings that result from the variation of the ambient temperature. Measurements 800 and 900 have areas with similar shapes (marked 850), having in some cases different scale, for the ambient temperature measurements 900 and for the reference temperature 800 as measured by the thermal image sensor 250. Measurements 800 and 900 have areas with differing shapes (marked 870). These readings result from changes of the thermal image sensor and are not correlated with the ambient temperature of scene 110. Analyzing the readings 800 and 900 from the ambient temperature of scene 110 and from reading from the thermal image sensor 250 of the same scene 110, enables evaluation of the parameter α. Example analysis methods include utilizing regression, least mean squares or by other numerical approaches on measurements 800 and 900. The detection of areas 850 and 870 can be performed, for example, by deep learning methods or by other analytical approaches.

As a non-limiting example, we present here a way for calculation of the parameter α:

In this evaluation we suppose that the studied object is the reference object 140 itself and its temperature is the ambient temperature is expressed by the following equations:

$$T'obj\_k = Tamb\_k - \alpha \cdot Tamb\_k - f(Tamb\_k);$$

$$k = 1 \div N;$$

where k is the $k^{th}$ measurement set of both ambient temperature and the thermal image sensor 250 reading. These data sets can be used to calculate the parameter α. For example, it can be done as a calculation of a slope of regression in a function where the T'obj_k represents the y-axis value and Tamb_k represents the argument values. In case that f(Tamb_k) is embedded in the reading of the thermal image sensor 250, the function f(Tamb_k)=0.

Figures 7A, 7B:
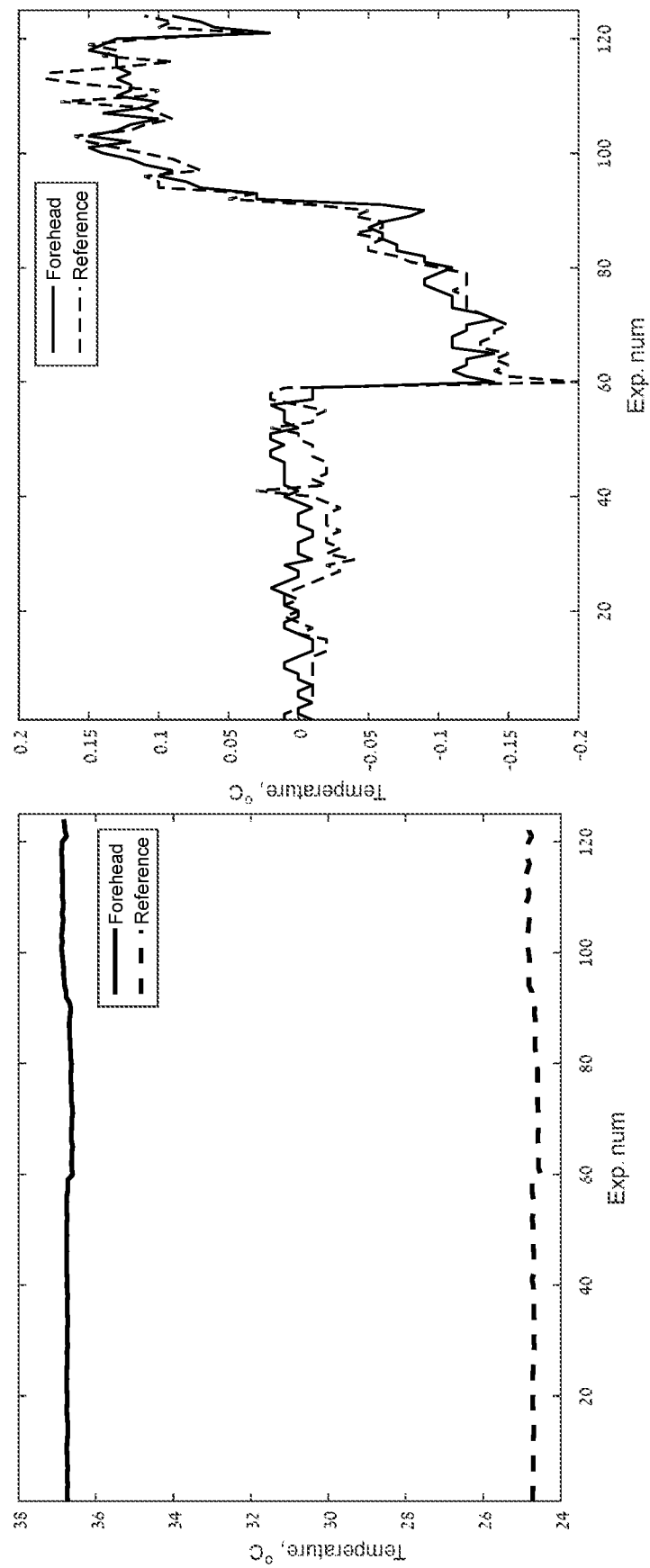
FIG. 7A is a non-limiting example of a graph representing temperature measurements as measured by the system.
FIG. 7B is a non-limiting example of the graph of FIG. 7A after subtraction of graph averages.

The above exemplary mathematical expression can provide a correction of the offset shift in the thermal image sensor 250. FIG. 7A shows a non-limiting example of a simultaneous change in the temperature measuring by the thermal image sensor 250 on a human's forehead and on reference object 140. The results shown in FIG. 7B are the results of FIG. 7A, after subtraction of graph averages, thus allowing for better understanding of the correlation between the shift in the human's forehead temperature and the shift reference object 140 temperature. The offset shift in the reference temperature measuring can be used for the correction of the body temperature measuring. In some cases, the correction expression can take into account effects of emissivity.

The scene ambient temperature can be obtained by system 200 at any phase of process 300. Scene ambient temperature can be measured by a temperature sensor that is part of system 200 or by a sensor that is external to system 200.

As explained above, the temperature of reference object 140 is expected to be the scene ambient temperature or dependent on the scene ambient temperature on a known regularity. As thermal image sensor 250 can be out of calibration, for example: thermal image sensor 250 was calibrated in one point in time but has gone out of calibration over time, there may be a difference between the reference temperature—being the temperature of reference object 140 as measured by thermal image sensor 250, and the actual temperature of reference object 140, being the scene ambient temperature obtained by system 200. System 200 can utilize the RoI temperatures to compensate for the difference, if any, and determine a corrected RoI temperature. System 200 can be configured to constantly calibrate thermal image sensor 250 utilizing reference object 140. The reference temperature knowledge also assists in reducing overall thermal sensor noise by utilizing noisy shift of the temperature measurement sensed by thermal image sensor 250.

Continuing the non-limiting example from above, system 200 obtains an indication that the scene ambient temperature of scene 110 is 24 degrees Celsius. Therefore, there is a +2 degrees Celsius difference between the reference temperature and the scene ambient temperature. System 200 uses the difference to determine the corrected temperature of RoI A 130-*a* to be 38 degrees Celsius. Thus, subject's A 120-*a* temperature is actually indicative of a body temperature that exceed a threshold of temperature that are considered as healthy.

In some cases, the correction of the RoI temperatures can be also based on a distance of the respective subject (e.g. subject A 120-*a*, subject B 120-*b*, subject C 120-*c*) from the thermal image sensor 250. In these cases, system 200 can use a moisture measuring device to obtain indication of the ambient moisture level and the effect of the moisture on the thermal radiation received by thermal image sensor 250 is associated with the distance of the subject (e.g. subject A 120-*a*, subject B 120-*b*, subject C 120-*c*) from the thermal image sensor 250. In some cases, moisture within scene 110 can affect the absorption of the IR radiation and thereby cause a variation of the temperature measured by the thermal image sensor 250 as a function of distance between the thermal image sensor 250 and the subject (e.g. subject A 120-*a*, subject B 120-*b*, subject C 120-*c*). Thus, the correction of the RoI temperatures is dependent on the distance between the thermal image sensor 250 and the subject (e.g. subject A 120-*a*, subject B 120-*b*, subject C 120-*c*). This correction can provide high accuracy temperature measurements.

Optionally, system 200 can further configured to alert an operator of the system upon identifying subjects (e.g. subject A 120-*a*, subject B 120-*b*, subject C 120-*c*) associated with corrected RoI temperatures exceeding a threshold (block 360).

Continuing the above non-limiting example, an operator of system 200 can be looking on a screen of system 200 displaying the visible spectrum image and an indication that subject's A 120-*a* temperature exceeds 37.5 degrees Celsius.

It is to be noted that, with reference to FIG. 3, some of the blocks can be integrated into a consolidated block or can be broken down to a few blocks and/or other blocks may be added. Furthermore, in some cases, the blocks can be performed in a different order than described. It is to be further noted that some of the blocks are optional. It should be also noted that whilst the flow diagram is described also with reference to the system elements that realizes them, this is by no means binding, and the blocks can be performed by elements other than those described herein.

FIG. 4, is a flowchart illustrating one example of a sequence of operations carried out for respiratory rate determination, in accordance with the presently disclosed subject matter.

According to certain examples of the presently disclosed subject matter, system 200 can be further configured to perform a respiratory rate determination process 400, e.g. utilizing the respiratory rate determination management module 280.

For this purpose, system 200 can be configured to obtain a sequence of subsequent visible spectrum images captured by the visible spectrum camera 240 subsequently to the visible spectrum image and a sequence of subsequent thermal images captured by the thermal image sensor 250 subsequently to the thermal image (block 410). A non-limiting example can be a first sequence of visible spectrum images wherein RoI B 130-*b* is the area of the nostrils of subject B 120-*b* and is visible in the first sequence and a second sequence of thermal images wherein RoI B 130-*b* is visible.

After obtaining the first sequence and the second sequence, system 200 can be further configured to register the subsequent visible spectrum images and the subsequent thermal images onto the common coordinate system (block 420). The registration allows a pixel-to-pixel translation between the pixels of the first sequence of visible spectrum images and pixels of corresponding thermal images of the second sequence.

After registering the images onto the common coordinate system, system 200 can be further configured to identify subsequent RoI pixels, on the common coordinate system, of the RoIs (e.g. RoI A 130-*a*, RoI B 130-*b*, RoI C 130-*c*) of the subjects (e.g. subject A 120-*a*, subject B 120-*b*, subject C 120-*c*) within the subsequent visible spectrum images (block 430). In our non-limiting example, the RoI pixels are the pixels of RoI B 130-*b* which are pixels in the area of the nostrils of subject B 120-*b* who is a human being.

After identifying the RoI pixels, system 200 can be further configured to track the subsequent RoI pixels within the subsequent thermal images of the thermal images sequence. System 200 can track the subsequent RoI pixels within the subsequent thermal images of the thermal images sequence by utilizing the respective subsequent visible spectrum images of the visible spectrum images sequence (block 440). System 200 utilizes the subsequent visible spectrum images of the first sequence for the tracking by using known tracking algorithms. The tracking is done by determining the location of the pixels of the RoIs (e.g. RoI A 130-*a*, RoI B 130-*b*, RoI C 130-*c*) in the subsequent visible spectrum images of the visible spectrum images sequence. The system determines the location of the RoIs within each image of the pairs of images of this sequence and thus is able to track the RoI along the sequence of images. In some cases, system 200 tracks the subsequent RoI pixels within the subsequent thermal images of the second sequence without usage of the first sequence.

System 200 can be further configured to determine a respiratory rate, which is the number of breaths a subject (e.g. one of: subject A 120-*a*, subject B 120-*b*, subject C 120-*c*) takes per minute, of the respective subject (e.g. one of: subject A 120-*a*, subject B 120-*b*, subject C 120-*c*) by analyzing the tracked subsequent RoI pixels for changes in temperature that occur as the respective subject (e.g. one of: subject A 120-*a*, subject B 120-*b*, subject C 120-*c*) exhales air (block 450). System 200 can also determine additional temporal information associated with the respiratory rate, such as: inhale time, exhale time, inhale to exhale time ration, etc.

Figure 6B:
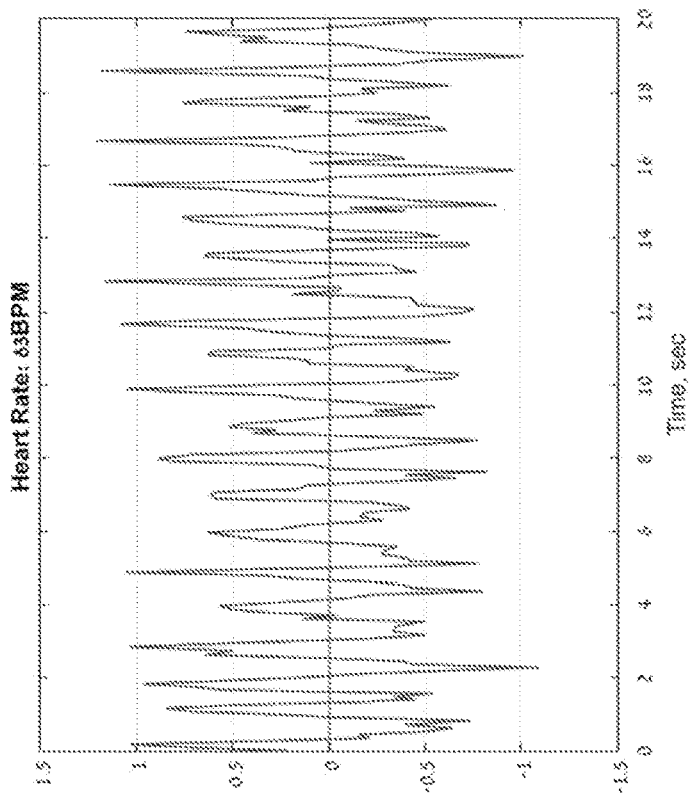
FIG. 6B is a non-limiting example of a graph representing pulse as measured by the system.
Figure 6A:
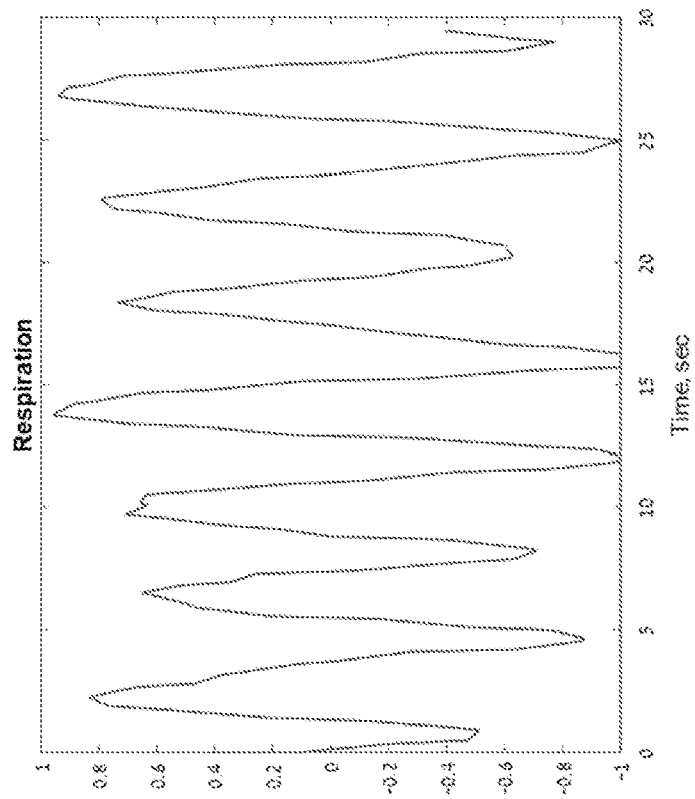
FIG. 6A is a non-limiting example of a graph representing respiratory rate as measured by the system.

Continuing the non-limiting example above, system 200 can determine the respiratory rate of subject B 120-*b* to be 15 breaths per minute, which is within the normal respiration rate range for an adult human being. FIG. 6A is a non-limiting example of a graph representing respiratory rate of a given subject (e.g. one of: subject A 120-*a*, subject B 120-*b*, subject C 120-*c*) as measured by system 200 over a given period of time.

It is to be noted that, with reference to FIG. 4, some of the blocks can be integrated into a consolidated block or can be broken down to a few blocks and/or other blocks may be added. Furthermore, in some cases, the blocks can be performed in a different order than described. It is to be further noted that some of the blocks are optional. It should be also noted that whilst the flow diagram is described also with reference to the system elements that realizes them, this is by no means binding, and the blocks can be performed by elements other than those described herein.

Turning to FIG. 5, there is shown a flowchart illustrating one example of a sequence of operations carried out for pulse determination, in accordance with the presently disclosed subject matter.

According to certain examples of the presently disclosed subject matter, system 200 can be further configured to perform a pulse determination process 500, e.g. utilizing the pulse determination management module 290.

For this purpose, system 200 can be configured to obtain a sequence of subsequent visible spectrum images captured by the visible spectrum camera subsequently to the visible spectrum image (block 510).

A non-limiting example can be a sequence of visible spectrum images wherein RoI C 130-*c* is the area of the forehead of subject C 120-*c* who is an adult human being and is visible therein.

After obtaining the sequence, system 200 can be further configured to track the RoI (e.g. RoI A 130-*a*, RoI B 130-*b*, RoI C 130-*c*) within the subsequent visible spectrum images of the sequence (block 520). System 200 utilizes the subsequent visible spectrum images of the third sequence for the tracking by using known tracking algorithms.

After tracking the RoI (e.g. RoI A 130-*a*, RoI B 130-*b*, RoI C 130-*c*), system 200 can be further configured to determine a pulse of the respective subject (e.g. one of: subject A 120-*a*, subject B 120-*b*, subject C 120-*c*) by analyzing changes of color within the RoI (e.g. one of: RoI A 130-*a*, RoI B 130-*b*, RoI C 130-*c*). The changes of color are due to the blood flowing through the veins in accordance with the cardiac cycle of the respective subject (e.g. one of: subject A 120-*a*, subject B 120-*b*, subject C 120-*c*) (block 530).

Continuing the non-limiting example above, system 200 can determine the pulse rate of subject C 120-*c* to be 80 beats per minute, which is within the normal resting heart rate range for an adult human being, based on the changes of color of RoI C 130-*c* within the third sequence. FIG. 6B is a non-limiting example of a graph representing pulse rate of a subject (e.g. one of: subject A 120-*a*, subject B 120-*b*, subject C 120-*c*) as measured by the system 200 over a given period of time.

It is to be noted that, with reference to FIG. 5, some of the blocks can be integrated into a consolidated block or can be broken down to a few blocks and/or other blocks may be added. Furthermore, in some cases, the blocks can be performed in a different order than described. It is to be further noted that some of the blocks are optional. It should be also noted that whilst the flow diagram is described also with reference to the system elements that realizes them, this is by no means binding, and the blocks can be performed by elements other than those described herein.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

It will also be understood that the system according to the presently disclosed subject matter can be implemented, at least partly, as a suitably programmed computer. Likewise, the presently disclosed subject matter contemplates a computer program being readable by a computer for executing the disclosed method. The presently disclosed subject matter further contemplates a machine-readable memory tangibly embodying a program of instructions executable by the machine for executing the disclosed method.

The invention claimed is:

1. A system for measuring temperature of one or more subjects within a scene including a reference object having an unknown emissivity, having an ambient temperature, the system comprising:
   a visible spectrum camera capable of acquiring images of the scene comprising (a) at least a Region of Interest (RoI) of each of the subjects, and (b) the reference object;
   a thermal image sensor capable of acquiring images of the scene comprising (a) at least the RoI of each of the subjects, and (b) the reference object; and
   a processing circuitry configured to:
      obtain (a) a visible spectrum image captured by the visible spectrum camera, and (b) a thermal image captured by the thermal image sensor, and (c) an indication of a scene ambient temperature within the scene;
      register the visible spectrum image and the thermal image onto a common coordinate system;
      identify (a) RoI pixels, on the common coordinate system, of the RoIs of the subjects within the visible spectrum image, and (b) reference object pixels, on the common coordinate system, of the reference object within the visible spectrum image;
      determine (a) RoI temperatures by analyzing respective RoIs pixels on the thermal image, (b) a reference temperature by analyzing the reference object pixels on the thermal image, and (c) a parameter correlated to an emissivity of the reference object, based on the reference temperature and on the indication of the scene ambient temperature; and
      upon existence of a difference between the reference temperature and the scene ambient temperature, correct the RoI temperatures, based on the difference and utilizing the parameter, to compensate for the difference, giving rise to corrected RoI temperatures.

2. The system of claim 1, wherein the determination of the parameter correlated to the emissivity of the reference object is performed by analyzing the reference temperature and the indication of the scene ambient temperature at a plurality of point in time during a given time period.

3. The system of claim 1, further comprising a three-dimensional (3D) camera capable of acquiring images of the scene comprising (a) at least a Region of Interest (RoI) of each of the subjects, and (b) the reference object, and wherein the processing circuitry is further configured to:
   obtain a depth image captured by the 3D camera; and
   utilize the depth image for the registration of the visible spectrum image and the thermal image onto the common coordinate system.

4. The system of claim 3, wherein the correction of the RoI temperatures is also based on at least one of: (a) a distance of the respective subject from the thermal image sensor determined based on the analysis of the depth image, or (b) on ambient moisture level.

5. The system of claim 1, wherein the reference object is diffusive and not specular.

6. The system of claim 1, wherein the processing circuitry is further configured to alert an operator of the system upon identifying subjects associated with corrected RoI temperatures exceeding a threshold.

7. The system of claim 1, wherein the reference object is made of material which temperature changes in a known manner according to changes to the scene ambient temperature.

8. The system of claim 1, wherein the RoI is an area affected by breathing of the respective subject and wherein the processing circuitry is further configured to:
   obtain (a) a first sequence of subsequent visible spectrum images captured by the visible spectrum camera subsequently to the visible spectrum image, and (b) a second sequence of subsequent thermal images captured by the thermal image sensor subsequently to the thermal image;
   register the subsequent visible spectrum images and the subsequent thermal images onto the common coordinate system;
   identify subsequent RoI pixels, on the common coordinate system, of the RoIs of the subjects within the subsequent visible spectrum images;
   track the subsequent RoI pixels within the subsequent thermal images of the second sequence utilizing the respective subsequent visible spectrum images of the first sequence; and
   determine a respiratory rate of the respective subject by analyzing the tracked subsequent RoI pixels.

9. The system of claim 1, wherein the RoI is a forehead of the respective subject and wherein the processing circuitry is further configured to:
   obtain a third sequence of subsequent visible spectrum images captured by the visible spectrum camera subsequently to the visible spectrum image;
   track the RoI within the subsequent visible spectrum images of the third sequence; and
   determine a pulse of the respective subject by analyzing changes of color within the RoI.

10. The system of claim 1, wherein the reference object includes one or more symbols visible to the visible spectrum camera or to the thermal image sensor and wherein the reference object pixels are identified using at least one of the symbols.

11. A method for measuring temperature of one or more subjects within a scene including a reference object having an unknown emissivity, having an ambient temperature, the method comprising:

obtaining, by a processing circuitry, (a) a visible spectrum image captured by a visible spectrum camera capable of acquiring images of the scene comprising at least a Region of Interest (RoI) of each of the subjects, and the reference object, and (b) a thermal image captured by a thermal image sensor capable of acquiring images of the scene comprising at least the RoI of each of the subjects, and the reference object, and (c) an indication of a scene ambient temperature within the scene;

registering, by the processing circuitry, the visible spectrum image and the thermal image onto a common coordinate system;

identifying, by the processing circuitry, (a) RoI pixels, on the common coordinate system, of the RoIs of the subjects within the visible spectrum image, and (b) reference object pixels, on the common coordinate system, of the reference object within the visible spectrum image;

determining, by the processing circuitry, (a) RoI temperatures by analyzing respective RoIs pixels on the thermal image, (b) a reference temperature by analyzing the reference object pixels on the thermal image and (c) a parameter correlated to an emissivity of the reference object, based on the reference temperature and on the indication of the scene ambient temperature; and upon existence of a difference between the reference temperature and the scene ambient temperature, correcting, by the processing circuitry, the RoI temperatures, based on the difference and utilizing the parameter, to compensate for the difference, giving rise to corrected RoI temperatures.

12. The method of claim 11, wherein the determination of the parameter correlated to the emissivity of the reference object is performed by analyzing the reference temperature and the indication of the scene ambient temperature at a plurality of point in time during a given time period.

13. The method of claim 11, further comprising:
obtaining, by the processing circuitry, a depth image captured by a three-dimensional (3D) camera capable of acquiring images of the scene comprising (a) at least a Region of Interest (RoI) of each of the subjects, and (b) the reference object; and
utilizing, by the processing circuitry, the depth image for the registration of the visible spectrum image and the thermal image onto the common coordinate system.

14. The method of claim 13, wherein the correction of the RoI temperatures is also based on at least one of: (a) a distance of the respective subject from the thermal image sensor determined based on the analysis of the depth image, or (b) on ambient moisture level.

15. The method of claim 11, wherein the reference object is diffusive and not specular.

16. The method of claim 11, wherein the reference object is made of material which temperature changes in a known manner according to changes to the scene ambient temperature.

17. The method of claim 11, wherein the RoI is an area affected by breathing of the respective subject and wherein method further comprising:
obtaining, by the processing circuitry, (a) a first sequence of subsequent visible spectrum images captured by the visible spectrum camera subsequently to the visible spectrum image, and (b) a second sequence of subsequent thermal images captured by the thermal image sensor subsequently to the thermal image;

registering, by the processing circuitry, the subsequent visible spectrum images and the subsequent thermal images onto the common coordinate system;

identifying, by the processing circuitry, subsequent RoI pixels, on the common coordinate system, of the RoIs of the subjects within the subsequent visible spectrum images;

tracking, by the processing circuitry, the subsequent RoI pixels within the subsequent thermal images of the second sequence utilizing the respective subsequent visible spectrum images of the first sequence; and determining, by the processing circuitry, a respiratory rate of the respective subject by analyzing the tracked subsequent RoI pixels.

18. The method of claim 11, wherein the RoI is a forehead of the respective subject and wherein the method further comprising:
obtaining, by the processing circuitry, a third sequence of subsequent visible spectrum images captured by the visible spectrum camera subsequently to the visible spectrum image;
tracking, by the processing circuitry, the RoI within the subsequent visible spectrum images of the third sequence; and
determining, by the processing circuitry, a pulse of the respective subject by analyzing changes of color within the RoI.

19. The method of claim 11, wherein the reference object includes one or more symbols visible to the visible spectrum camera or to the thermal image sensor and wherein the reference object pixels are identified using at least one of the symbols.

20. A non-transitory computer readable storage medium having computer readable program code embodied therewith, the computer readable program code, executable by at least one processing circuitry of a computer to perform a method for measuring temperature of one or more subjects within a scene including a reference object having an unknown emissivity, having an ambient temperature, the method comprising:
obtaining, by a processing circuitry, (a) a visible spectrum image captured by a visible spectrum camera capable of acquiring images of the scene comprising at least a Region of Interest (RoI) of each of the subjects, and the reference object, and (b) a thermal image captured by a thermal image sensor capable of acquiring images of the scene comprising at least the RoI of each of the subjects, and the reference object, and (c) an indication of a scene ambient temperature within the scene;
registering, by the processing circuitry, the visible spectrum image and the thermal image onto a common coordinate system;
identifying, by the processing circuitry, (a) RoI pixels, on the common coordinate system, of the RoIs of the subjects within the visible spectrum image, (b) reference object pixels, on the common coordinate system, of the reference object within the visible spectrum image and (c) a parameter correlated to an emissivity of the reference object, based on the reference temperature and on the indication of the scene ambient temperature;
determining, by the processing circuitry, (a) RoI temperatures by analyzing respective RoIs pixels on the thermal image, and (b) a reference temperature by analyzing the reference object pixels on the thermal image; and upon existence of a difference between the reference temperature and the scene ambient temperature, correcting, by the processing circuitry, the RoI temperatures, based on the difference and utilizing the parameter, to compensate for the difference, giving rise to corrected RoI temperatures.

* * * * *